United States Patent [19]

Kominami et al.

[11] 3,932,549

[45] Jan. 13, 1976

[54] PROCESS FOR PREPARING TERT-BUTYLSTYRENE

[75] Inventors: Naoya Kominami, Tokyo; Nobuhiro Tamura, Oimachi, both of Japan

[73] Assignee: Asahi Kasei Kogyo Kabushiki Kaisha, Japan

[22] Filed: July 12, 1971

[21] Appl. No.: 161,886

[30] Foreign Application Priority Data

May 10, 1971 Japan................................ 46-30470

[52] U.S. Cl. ........................ 260/669 R; 260/671 A
[51] Int. Cl.$^2$...................... C07C 3/52; C07C 15/02
[58] Field of Search............. 260/671 A, 671 C, 669

[56] References Cited
FOREIGN PATENTS OR APPLICATIONS
1,961,722  6/1970  Germany Primary Examiner—C. Davis
Attorney, Agent, or Firm—Cushman, Darby & Cushman

[57] ABSTRACT tert-Butylstyrene is prepared by a one-step reaction of tert-butylbenzene, ethylene and oxygen in the presence of a catalyst prepared by treating metallic palladium or fatty acid salts thereof with pyridine. The yield is increased by using together therewith a promoter prepared by treating one or more metals or oxides or fatty acid salts thereof, the metals being selected from the group consisting of copper, nickel, manganese, uranium and thallium. The reaction is carried out at a temperature between 50° to 300°C under a pressure of up to 100 kg/cm$^2$.

4 Claims, No Drawings

PROCESS FOR PREPARING TERT-BUTYLSTYRENE

This invention relates to a process for preparing tert-butylstyrene, and more particularly, it concerns a process for preparing tert-butylstyrene by a one-step reaction of tert-butylbenzene, ethylene and oxygen.

tert-Butylstyrene is useful as a comonomer for preparing copolymers or as a curing agent for fibre-reinforced plastics because it has such effects as lessening the mold shrinkage of molded articles and improving the moldability of plastics.

It has only been known to prepare tert-butylstyrene by tertiary-butylating ethylbenzene with butanol followed by dehydrogenation thereof. The process mentioned above, however, is not suitable for commercial preparation, because its yield and selectivity are very low and the starting materials are very expensive. Moreover, separation of the product is extremely difficult.

The present inventors have now found that the use of a specific palladium catalyst enables the one-step preparation of tert-butylstyrene by subjecting tert-butylbenzene, ethylene and oxygen to reaction.

An object of the present invention is to provide a method for the one-step preparation of tert-butylstyrene using a specific palladium catalyst. Another object of the present invention is to provide a process for preparing tert-butylstyrene in high yield and in high selectivity.

The present invention, therefore, provides a process for a method for the one-step preparation of tert-butylstyrene which comprises reacting tert-butylbenzene with ethylene and oxygen in the presence of a catalyst prepared by treating metallic palladium or a fatty acid salt thereof with pyridine with or without a promoter prepared by treating one or more metals selected from copper, nickel, manganese, uranium and thallium, or fatty acid salts or oxides thereof, with pyridine.

The catalyst is prepared by treating metallic palladium or a fatty acid salt of palladium with a pyridine solution or by adding pyridine to a catalyst layer of metallic palladium or fatty acid salt of palladium before the reaction. As the metallic palladium, that prepared by reducing palladium salts may be used. As the fatty acid salt of palladium, palladium acetate or palladium propionate is preferable.

As the promoter, metallic copper, nickel, manganese, uranium or thallium or oxides or fatty acid salts of these metals may be used. Among the fatty acid salts of these metals, acetates, formates or propionates of these metals are preferable. These metals or oxides or fatty acid salts thereof may be used alone or in combination of two or more. The promoter is also required to be treated with pyridine.

The promoter can be used in a proportion of M/Pd of 1,000 – 1/200 (in atomic ratio), preferably 50 – 1/50, wherein M is the metal of promoter mentioned above.

The catalyst with or without the promoter can be supported on a carrier. As the carrier, active carbon, silica or alumina is preferable. When catalyst supported on a carrier is required, it can be prepared by supporting a promoter on the carrier first, treating the assembly at a high temperature, and then supporting palladium or a fatty acid salt of palladium on the same. The thus obtained catalyst is treated with pyridine. An example of preparing such catalyst is as follows: manganese nitrate is supported on silica gel, which is then calcined at 500°C for 10 hours to produce manganese oxide-silica gel. Then, palladium and pyridine are supported on said manganese oxide-silica gel.

The use of a promoter with the palladium catalyst is favorable in the process of the present invention because of its increasing the yield of tert-butylstyrene by about two to 10 times or more.

In the process of the present invention, temperatures between 50° and 300°C, preferably 80° to 250°C may be employed.

The reaction may be carried out at ordinary pressure, more preferably under a pressure of up to 100 kg/cm$^2$.

Ethylene and oxygen are used in the reaction in a proportion of 10 – 0.01 moles of ethylene per mole of oxygen. Instead of pure oxygen, a mixture of oxygen and inert gases such as nitrogen, carbon dioxide, etc. which do not affect the reaction, may be used. It is advantageous to use 3 – 1/50 moles of ethylene per mole of tert-butylbenzene.

The use of an organic acid such as acetic acid, propionic acid, and the like in the process of the present invention is preferable, but not essential. Said organic acid is preferably used in an amount of less than double the molar quantity of the tert-butylbenzene.

The reaction of the present invention may be carried out with a reaction process such as flow method, a method of stirring a mixture of gas and liquid, gas-blowing method, etc. The reaction can take place both in gas phase and liquid phase.

In order that the invention may be more fully understood, the following Examples are given, by way of illustration only:

EXAMPLE 1

A catalyst was prepared by dissolving 0.1 g of palladium in 10 ml. of pyridine, adding 10 ml. of silica gel particles to the solution, and evaporating the mixture to dryness. The obtained catalyst (10 ml.), 20 ml. of tert-butylbenzene, and 10 ml. of acetic acid were enclosed in a microbomb having an inner volume of 50 ml., and ethylene and oxygen were introduced into the bomb in terms of a pressure of 10 kg/cm$^2$ and 30 kg/cm$^2$, respectively, from the upper valve. The reaction was carried out at 150°C for 5 hours with laying said bomb in an oil bath equipped with a shaking means. tert-Butylstyrene was yielded in a proportion of 470 %, based on the mole of palladium in the used catalyst. No by-product was detected.

EXAMPLE 2

A catalyst was prepared by dissolving 1.8 g of palladium chloride in diluted hydrochloric acid, adding 100 ml. of silica gel particles to the solution, evaporating the mixture to dryness, adding 50 ml. of alkaline hydrazine hydrate to the resulting mixture to reduce palladium chloride, washing the resulting mixture with water sufficiently, and drying the same at 150°C for one day. To the thus obtained catalyst (10 ml.) was added 1 ml. of pyridine, and the resulting mixture was enclosed together with 20 ml. of tert-butylbenzene, and 2 ml. of acetic acid in a microbomb having an inner volume of 50 ml., and ethylene and oxygen were introduced into the bomb in terms of a pressure of 10 kg/cm$^2$ and 20 kg/cm$^2$, respectively, from the upper valve. The reaction was carried out at 170°C for 3 hours. tert-Butylstyrene was yielded in a proportion of 340 %, based on the mole of palladium in the catalyst used.

COMPARATIVE EXAMPLE

Example 2 was repeated except that no pyridine was added before the reaction. tert-Butylstyrene was yielded in a proportion of 190 %, based on the mole of palladium in the catalyst used.

EXAMPLE 3

A catalyst was prepared by dissolving 0.1 g of palladium propionate in 10 ml. of pyridine, adding 10 ml. of alumina particles to the solution, and evaporating the mixture to dryness. The thus obtained catalyst (10 ml.), 10 ml. of tert-butylbenzene and 1 ml. of acetic acid were enclosed in a microbomb having an inner volume of 50 ml., and ethylene and oxygen were introduced into the bomb in terms of a pressure of 20 kg/cm$^2$ and 50 kg/cm$^2$, respectively, from the upper valve. The reaction was carried out at 130°C for 10 hours. tert-Butylstyrene was yielded in a proportion of 350 %, based on the mole of palladium in the catalyst used. A trace of tert-butylbenzaldehyde was detected.

EXAMPLE 4

A catalyst was prepared by dissolving 0.1 g of palladium acetate and 0.2 g of manganese acetate in 10 ml. of pyridine, adding 10 ml. of silica gel particles to the solution, and evaporating the mixture to dryness. The thus obtained catalyst (10 ml.), 20 ml. of tert-butylbenzene and 3 ml. of acetic acid were enclosed in a microbomb having an inner volume of 50 ml., and ethylene and oxygen were introduced into the bomb in terms of a pressure of 10 kg/cm$^2$ and 30 kg/cm$^2$, respectively, from the upper valve. The reaction was carried out at 150°C for 5 hours. tert-Butylstyrene was yielded in a proportion of 1820 %, based on the mole of palladium in the catalyst used. No by-product was detected.

EXAMPLE 5

To an aqueous solution containing 0.5 g of manganese nitrate was added 10 ml. of silica gel particles. After being evaporated to dryness, the mixture was calcined at 450°C for 10 hours. The thus obtained silica gel was immersed in 10 ml. of pyridine solution containing dissolved therein 0.02 g of palladium propionate and 0.1 g of uranium acetate, and then evaporated to dryness to obtain a catalyst. The catalyst (10 ml.), 10 ml. of tert-butylbenzene and 1 ml. of acetic acid were enclosed in a similar bomb to that used in Example 4, and etylene and oxygen were introduced into the bomb both in terms of a pressure of 20 kg/cm$^2$ from the upper valve. The reaction was carried out at 140°C for 10 hours with shaking. tert-Butylstyrene was yielded in a proportion of 1200 %, based on the mole of palladium in the catalyst used.

EXAMPLE 6

A catalyst solution was prepared by dissolving 0.05 g of palladium acetate, 0.02 g of cupric acetate and 0.02 g of thallium acetate in 1 ml. of pyridine and adding thereto 10 ml. of acetic acid. Said catalyst solution and 20 ml. of tert-butylbenzene were enclosed in a microbomb having a volume of 100 ml. and ethylene and oxygen were introduced into the bombe in terms of pressure of 10 kg/cm$^2$ and 30 kg/cm$^2$, respectively, from the upper valve. The reaction was carried out at 120°C for 16 hours laying said bomb in an oil bath equipped with a shaking means. tert-Butylstyrene was yielded in a proportion of 1500 %, based on the mole of palladium in the catalyst used.

EXAMPLE 7

A catalyst (10 ml.) prepared by a similar method to that in Example 4 was charged into a vertical reaction tube of hard glass and heated at 180°C., after which a mixed solution of tert-butylbenzene and acetic acid in a proportion of 9 moles of the former per mole of the latter was introduced into the reaction tube from its upper part at a rate of 10 ml./min, while a mixed gas of ethylene and oxygen in a proportion of 3 moles of the former per mole of the latter was introduced thereinto from the bottom at a rate of 30 ml./min. The liquid accumulated at the bottom of the reaction tube was analyzed, to find that tert-butylstyrene was yielded at a rate of 1.5 % based on tert-butylbenzene. The activity of the catalyst was not lowered even after 20 hours' reaction.

EXAMPLES 8 – 13

Catalysts, the compositions of which are as set forth in the following Table, were prepared by a similar method to that in Example 5. The reactions were carried out according to Example 5 except for the reaction conditions set forth in the Table. The results obtained were as set forth in the Table.

Table

| Example No. | Composition of the catalyst (g/10 ml of carrier) | | T.B.B.*$^1$ (ml) | Charging conditions Acetic acid (ml) | Ethylene (kg/cm$^2$) | Oxygen (kg/cm$^2$) | Reaction temperature (°C) | Reaction time (hour) | Yield of T.B.S.*$^2$ (% based on Pd) |
|---|---|---|---|---|---|---|---|---|---|
| 8 | Pd(OAc)*$^3$ - Mn(OAc)- 0.05 Ni(O )/SiO$_2$*$^4$ | 0.05 | 15 | 1 | 10 | 30 | 150 | 5 | 2160 |
| 9 | Pd(OAc) - Tl(OAc)- 0.02 Mn(O)/SiO$_2$ 0.1 | 0.05 | 10 | 2 | 10 | 30 | 120 | 24 | 3800 |
| 10 | Pd(OAc) - Cu(OAc)- 0.05 Mn(O)/SiO$_2$ 0.3 | 0.02 | 10 | 2 | 10 | 30 | 120 | 3 | 1050 |
| 11 | Pd(OAc)-Mn(OAc)- 0.05 Ni(OAc)/Al$_2$O$_3$ 0.04 | 0.03 | 10 | 1 | 10 | 30 | 140 | 4 | 1290 |
| 12 | Pd(OAc)- 0.02 U(OAc)/SiO$_2$ 0.01 | | 15 | 3 | 10 | 30 | 160 | 5 | 960 |

Table-continued

| Example No. | Composition of the catalyst (g/10 ml of carrier) | T.B.B.*1 (ml) | Charging conditions Acetic acid (ml) | Ethylene (kg/cm²) | Oxygen (kg/cm²) | Reaction temperature (°C) | Reaction time (hour) | Yield of T.B.S.*2 (% based on Pd) |
|---|---|---|---|---|---|---|---|---|
| 13 | Pd(OAc)-Cu(OAc)- 0.05  0.02 Cu(O)/SiO₂ 0.1 | 10 | 10 | 10 | 30 | 130 | 5 | 1370 |

Note) *1 T.B.B. represents tert-butylbenzene
*2 T.B.S. represents tert-butylstyrene
*3 Pd(OAc) represents palladium acetate. Similar abbreviations are used for other metals.
*4 Ni(O) represents nickel oxide. Similar abbreviations are used for other metals.

What is claimed is:

1. A process for preparing tert. butyl styrene which comprises reacting tert. butyl benzene with 1/50 to 3 moles of ethylene and 1/500 to 300 moles of oxygen per mole of tert. butyl benzene at a temperature between 50° and 300°C. and at a pressure up to 100 kg/cm² in the presence of a catalyst prepared by treating metallic palladium or a fatty acid salt thereof with pyridine.

2. A process according to claim 1, wherein said catalyst contains at least one promoter selected from the group consisting of metallic copper, nickel, manganese, uranium and thallium, and oxides and fatty acid salts of these metals, said promoter being treated with pyridine.

3. A process according to claim 1, wherein the reaction is carried out in the presence of at least one organic acid.

4. A process according to claim 2, wherein the promoter is used in a proportion of M/Pd between 1,000 and 1/200 (in atomic ratio) in which M represents the metal of promoter.

* * * * *

UNITED STATES PATENT OFFICE
CERTIFICATE OF CORRECTION

Patent No. 3,932,549  Dated January 13, 1976

Inventor(s) NAOYA KOMINAMI, et al

It is certified that error appears in the above-identified patent and that said Letters Patent are hereby corrected as shown below:

Insert --[30] Foreign Application Priority Data

May 10, 1971 Japan   30410/71
    July 11, 1970 Japan  60467/70 --

Signed and Sealed this sixth Day of April 1976

[SEAL]

Attest:

RUTH C. MASON
*Attesting Officer*

C. MARSHALL DANN
*Commissioner of Patents and Trademarks*